United States Patent [19]

Hjertman

[11] Patent Number: 5,735,824

[45] Date of Patent: Apr. 7, 1998

[54] DEVICE FOR METERING AND ADMINISTERING A LIQUID PREPARATION

[75] Inventor: Birger Hjertman, Vällingby, Sweden

[73] Assignee: Pharmacia & Upjohn Aktiebolag, Stockholm, Sweden

[21] Appl. No.: 362,481

[22] PCT Filed: Apr. 22, 1994

[86] PCT No.: PCT/SE94/00360

§ 371 Date: Jan. 30, 1995

§ 102(e) Date: Jan. 30, 1995

[87] PCT Pub. No.: WO94/25091

PCT Pub. Date: Nov. 10, 1994

[30] Foreign Application Priority Data

Apr. 30, 1993 [SE] Sweden ............... 9301495

[51] Int. Cl.[6] .................................. A61M 5/00
[52] U.S. Cl. .................. 604/208; 604/134; 604/181; 604/218
[58] Field of Search .................. 222/339, 340; 604/131–135, 181, 186, 187, 218, 207–211, 224, 228, 232–234, 246

[56] References Cited

U.S. PATENT DOCUMENTS

| | | | |
|---|---|---|---|
| 4,254,767 | 3/1981 | Mixon, Jr. | 604/181 |
| 4,368,732 | 1/1983 | Cassou et al. | 604/181 |
| 4,589,870 | 5/1986 | Citrin et al. | 604/208 |
| 4,737,151 | 4/1988 | Clement et al. | 604/181 |
| 5,176,646 | 1/1993 | Kuroda | 604/131 |
| 5,228,883 | 7/1993 | Blakely et al. | 604/208 |

FOREIGN PATENT DOCUMENTS 2805513  9/1978  Germany ............... 604/221

Primary Examiner—Mark Bockelman
Assistant Examiner—Ronald K. Stright, Jr.
Attorney, Agent, or Firm—Pollack, Vande Sande & Priddy

[57] ABSTRACT

An injection device is provided for the infinitely variable metering and administering of a liquid preparation from a multi-dose injection cartridge having a rear piston which may be moved forward by means of a piston rod. The longitudinal movement of the piston rod is governed by two couplings arranged along the piston rod and each being capable of releasably gripping the piston rod by a locking device. The piston rod has a wedge-shaped cross section and each of the couplings includes a clamping shoe which has a wedge-shaped groove, the cross section of which is adapted to that of the piston rod, and locking device, by which the piston rod and each clamping shoe may be releasably clamped together to lock the piston rod in the groove of said clamping shoe.

19 Claims, 2 Drawing Sheets

DEVICE FOR METERING AND ADMINISTERING A LIQUID PREPARATION

TECHNICAL FIELD

The present invention is directed to a device for dosing and administering a liquid preparation. More specifically, the invention relates to repeated dosing and administering of liquid pharmaceutic preparations by parenteral injection from a multi-dose container. Still more specifically, the invention relates to a device for infinitely variable dosing and administering of liquid pharmaceutic preparation by parenteral injection from a multi-dose container, such as an injection cartridge.

BACKGROUND ART

In the International patent application PCT/SE92/00654 describes a method for repeated dosing of a liquid preparation of a pharmaceutically active agent by administration from a multi-dose container having a defined volume. What characterizes this method is that the amount of the preparation to be dosed is selected to be 1/N of the volume of the multi-dose container, N being an integer having a value of 2 or higher. The value of N is selected and set before the repeated dosing of the preparation from the multi-dose container is started, and is maintained unchanged through a series of N successive administrations from the multi-dose container, which has consequently then been emptied. As the other variable is used the concentration of the liquid preparation, such that the portion 1/N will give the desired dose of the pharmaceutically active agent. By using a series of containers with preparations of different concentrations, and a plurality of values for N, it is clear that a great number of different doses of the active agent can be obtained.

Through the method and system described, it has thus become possible to administer a number of doses of a liquid preparation from a multi-dose container in such a way that essentially no residue of the preparation is obtained. This is of considerable importance when very expensive pharmaceutical agents are to be administered, such as growth hormones.

The above-mentioned international application PCT/SE92/00654 also discloses a device for the repeated dosing of a liquid preparation from a multi-dose container. Such a device comprises a holder device for a multi-dose container having a defined volume and containing a preparation having a defined composition, and the multi-dose container is provided with a fixed front wall, through which may be arranged an outlet for the preparation, and a movable rear wall, which may act as a piston for expelling the preparation through said outlet, and a piston rod, by which the rear movable wall may be urged forwards. What characterizes the device is that the piston rod is provided with releasable blocking means by which the forward movement of it is limited to a predetermined length, which corresponds to a forward movement of the rear movable wall corresponding to 1/N of the multi-dose container, N being an integer having a value of 2 or higher.

It is to be noted that in the following specification and claims, the expressions "front" and "forward" refer to the direction in which the liquid preparation is made to flow when it is administered. Conversely, the opposite direction is denoted as "rear" and "rearward", respectively.

A preferred embodiment of the device described above, employs a barrel for holding at its front end part an injection cartridge and a piston rod for actuating the injection cartridge to expel a set amount of the liquid preparation from the cartridge.

The releasable blocking means comprise a fixed chuck and a movable chuck which clamp around the piston rod through the action of a spring force, the clamping action being releasable by reducing said spring force. Thus, the front chuck is fixed in relation to the barrel and the cartridge, and its clamping action around the piston rod may be actuated to lock it securely to the chuck, or may be released to allow the piston rod to move in relation to the chuck. The rear chuck is movable in relation to the barrel and the cartridge, and can be moved along the piston rod, when its clamping action is released, or may follow the piston rod in its movement, when the clamping action is actuated.

When a measured dose of the liquid preparation is to be administered, the rear chuck is moved rearwards against a spring force by means of a yoke arrangement, which at the same time releases the clamping action of the chuck such that it can move along the piston rod at the same time as said piston rod is locked in place by means of the clamping action of the front chuck. The rearward movement of the rear chuck is limited by stopping means, and the clamping action of this chuck is actuated again in this rear position, so that the chuck is locked in place in said rear position. The distance that the rear chuck is moved rearward is predetermined and set in the device, and determines the magnitude of the dose of the liquid preparation.

When a dose is to be administered, the clamping action of the front chuck is released. The spring force will now urge the rear chuck and the piston rod forward the same distance as that set for the rearward movement. Under the influence of the spring force, the piston rod will act on the rear movable wall of the injection cartridge to urge the movable wall forward to expel a metered dose of the liquid preparation from the cartridge.

These two readying and adminstering steps may then be repeated as many times as desired, until the cartridge has been emptied.

The important feature of the device described above is that the dose set can be infinitely varied. This is necessary for administering in accordance with the method described, where no residue should be left after administering a determined number of doses. This method and device should not be confused with the prior art methods and devices for administering liquid preparations. The prior art devices for repeated administration from a multi-dose cartridge usually consist of an injection device which comprises a mechanism for a stepwise forward movement of the rear movable wall of the injection cartridge, such as a screw or ratchet mechanism. The steps which are possible with this type of mechanism are fixed and a dose can only be determined by a given number of steps. Thus, the prior art mechanism may be adapted to the injection cartridge in such a manner that an advancement of the mechanism by one step will give a dosed amount of, for example, 1/8 of the volume of the cartridge. However, the mechanism cannot then be easily adapted to give a dose of, for example, 1/7, 1/9 or 1/10 of the volume of the cartridge. This means that only a limited number of dose amounts are possible without giving a residue.

In contrast to this, it will always be possible with the device described above to set a dose which is 1/N of the volume of the cartridge, N being an integer. The value of N may be set on the device before a series of administrations is started, and it should not then be easy to change unintentionally. By providing a suitable range of cartridges with varying concentrations of the preparation and a suitable range of values for N, it is possible to obtain a wide range of possible doses. This range of doses may then be presented in a table, from a computer memory, or in a nomograph, for easy reference by the physician.

The device described in the international patent application PCT/SE92/00654 has turned out to work well in the practice of the method described. However, there is room for some improvements. Thus, the arrangement of two separate chucks for alternately locking and releasing the piston rod is rather complicated. A considerable spring force is necessary to grip and lock the piston rod securely, and this also makes it necessary to use a considerable force when the chucks are to be released, such as when an injection is to be administered. This may make the administering difficult in those cases when the patient is to administer the injections to himself, such as in the ambulatory treatment of diabetes with insulin. After repeated use with a number of injection cartridges, this may also lead to wear on the piston rod, such that the accuracy of the metering of the dose will be decreased.

These disadvantages are eliminated by the injection device of the present invention.

SUMMARY OF THE INVENTION

According to the present invention, an injection device is provided for an infinitely variable metering and administering of a liquid preparation, and comprising a holder device for a multi-dose injection cartridge which comprises a fixed front wall through which may be arranged a liquid connection for discharging the preparation, and a rear, movable wall which may be moved forward by means of a piston rod to expel the preparation from the cartridge, the movement of the piston rod being governed by two couplings arranged along the length of the piston rod, each of the couplings being capable of releasably gripping and retaining the piston rod by means of locking means. The forward coupling is fixed in relation to the holder device and the injection cartridge, and the rear coupling may be moved rearwards along the piston rod against a spring pressure and again grip the piston rod in a rear position, after which the forward coupling may be released to free the piston rod such that the spring pressure will move the piston rod and the rear coupling locked thereto forward for a predetermined distance and thereby also move the rear movable wall of the injection cartridge forward to expel a predetermined amount of the liquid preparation from the cartridge. What characterizes the invention is that the piston rod has a wedge-shaped cross-section and that each of the couplings consists of a clamping shoe having a wedge-shaped groove, the cross-section of which is adapted to that of the piston rod, and lever means arranged in each clamping shoe, by means of which the piston rod and the clamping shoe may be clamped together to lock the piston rod in the groove of the clamping shoe, or the clamping shoe may be released from the piston rod to release the coupling.

BEST AND VARIOUS MODES FOR CARRYING OUT THE INVENTION

In a preferred embodiment, the holder device is provided with stopping means at its rear part, which restrict the rearward movement of the rear coupling, and the stopping means are adjustable in the longitudinal direction such that the rearward movement and thereby also the forward movement of the piston rod at the administering, may be set at a predetermined value.

In a further preferred embodiment, a yoke is provided for the rearward movement of the rear coupling, the yoke being connected to the rear coupling and its lever means in such a way that the coupling is released from the piston rod as it is moved rearwards and is again locked to the piston rod when the movement is terminated.

In a still further preferred embodiment, the lever means of the two couplings are spring loaded in such a manner that they strive to lock each of the couplings to the piston rod.

Preferably, the lever means comprise eccentric disks, which by being rotated may lock the couplings to the piston rod or release the couplings.

The device of the invention and its function will now be described in more detail, reference being made to the appended drawings.

Figure 1:
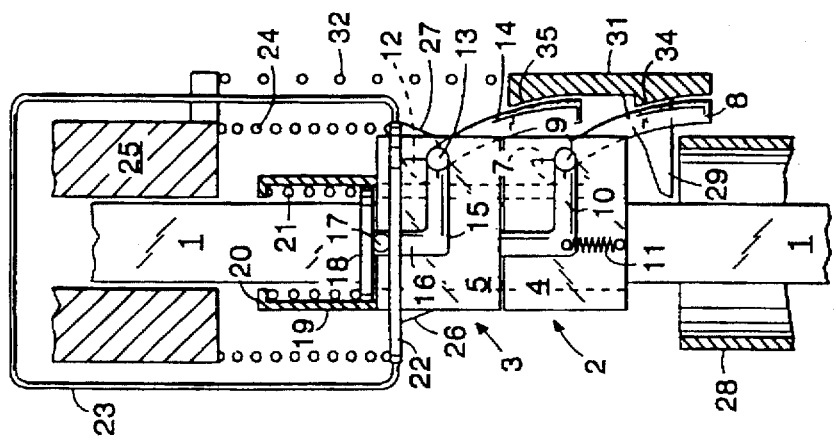
FIG. 1 illustrates the arrangement of the device before being readied for administering.
Figure 2:
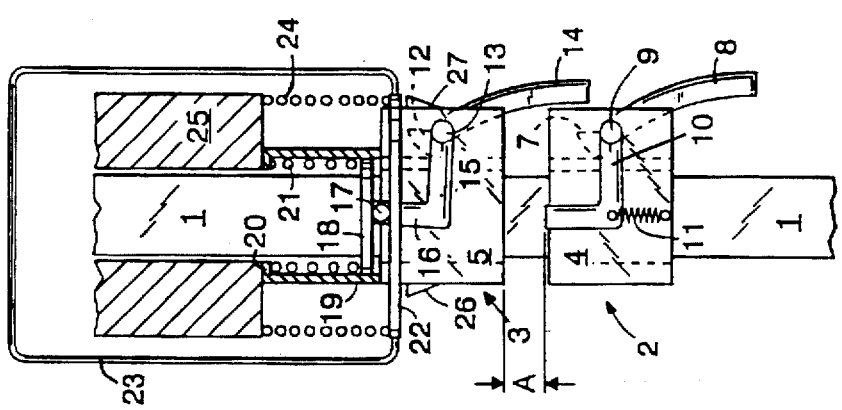
FIG. 2 illustrates the device after it has been readied for administering.
Figure 3:
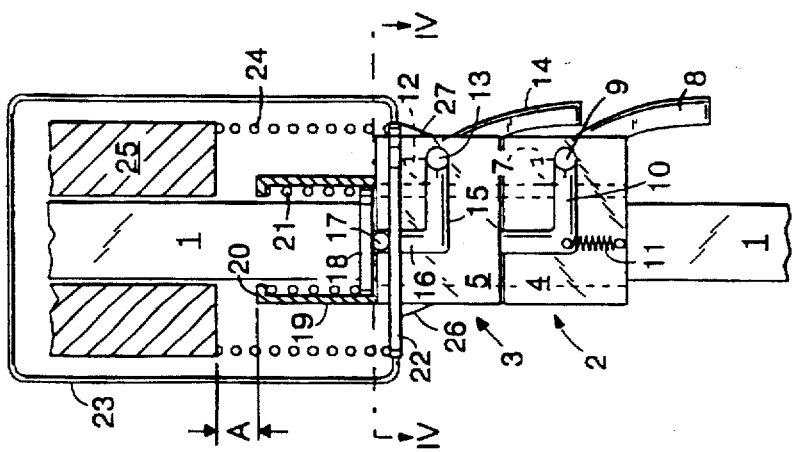
FIG. 3 illustrates the device after administering along with an arrangement for exchanging an emptied injection cartridge for a fresh one.
Figure 4:
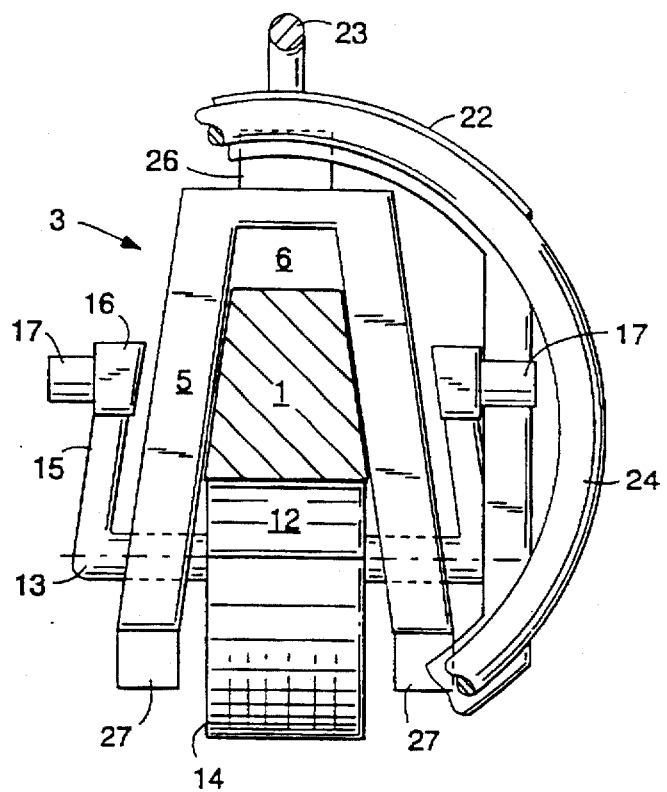
FIG. 4 is a partial sectional view taken along IV—IV in FIG. 1.

In the drawings, FIG. 1 shows the arrangement of the device before it has been readied for an administering. FIG. 2 shows the device after it has been readied for an administering. FIG. 3 shows the device after an administering has been made, and also an arrangement for exchanging an emptied injection cartridge for a fresh one. FIG. 4 is a partly sectional view along IV—IV in FIG. 1. In all figures, like parts have the same reference numbers.

It is to be noted that FIGS. 1 to 3 only show those parts of the injection device which characterize it in accordance with the present invention. Therefore, these drawing figures do not show the holder device for the injection cartridge or the injection cartridge as such, for example. The arrangement of these parts is conventional and apparent to a person skilled in the art.

FIG. 1 shows the piston rod 1 and the front coupling 2 and the rear coupling 3. The piston rod 1 has a wedge-shaped cross-section and is surrounded by the clamping shoe 4 of the front coupling 1, and by the clamping shoe 5 of the rear coupling 3. The two clamping shoes 4 and 5 each have a wedge-shaped longitudinal groove 6, the shape of which is adapted to the cross-sectional shape of the piston rod 1. This can be seen more clearly in FIG. 4. It will be seen that when the piston rod 1 is forced into the groove 6 of the clamping shoe 5, the coupling 3 and the piston rod 1 will be locked together and cannot move relative to each other. Because of the wedging effect, only a moderate force will be necessary for locking the couplings and the piston rod together, and this is an important advantage of the present invention. Also, the piston rod 1 and the clamping shoe 5 will only have to be displaced a very small distance relative to each other for a secure locking or release to take place.

The front coupling 2 is stationary in relation to the holder device and the injection cartridge of the device. The piston rod 1 may be forced into the groove of the clamping shoe 4 by means of an eccentric disk 7, which may be rotated around the axis 9. This axis 9 also serves as the fulcrum for lever means comprising an outer arm 8 and an inner arm 10, which both are solidly connected to the eccentric disk 7 and its axis 9. Thus, when the outer arm 8 is moved outwards, the eccentric disk 7 will turn about the axis 9 in such a way that the piston rod 1 is urged into the groove of the clamping shoe 4 to lock the piston rod 1 and the front coupling 2 securely together. A spring 11 acts on the inner arm 10 of the lever means, striving to pull it forward in the direction that the administering takes place, and thereby also to rotate the eccentric disk 7 to its locking position. This locking of the piston rod 1 together with the coupling 2 may be released by moving the outer lever arm 8 inward. This will also rotate the eccentric disk 7 in such a direction that the piston rod 1 is no longer forced into the groove of the clamping shoe 4, and the piston rod 1 will be released from the coupling 2. Preferably, there is one inner arm 10 with its spring 11 connected to each end of the axis 9, such that there is one lever arm 10 on each side of the clamping shoe 4.

The rear coupling 3 is arranged movable in the longitudinal direction along the piston rod 1. It comprises a clamping shoe 5 of a design similar to the front clamping shoe 4, having a wedge-shaped groove 6 with a cross-section adapted to that of the piston rod 1. An eccentric disk 12 can be rotated around the axis 13 by means of the outer lever arm 14 or the inner lever arm 15. When the outer lever arm 14 is moved outward, or the inner lever arm 15 is moved forward, the eccentric disk 12 will rotate in such a way that the piston rod 1 is forced into the groove 6 of the rear clamping shoe 5, to lock the rear coupling 3 to the piston rod. When the outer lever arm 14 is moved inward and the inner lever arm 15 is moved rearward, the eccentric disk 12 will rotate around the axis 13 in such a way that the piston rod 1 is released from the rear coupling 3.

The inner lever arm 15 has an extension 16 which is bent to point rearward. This rearward-pointing extension 16 is provided with a radial pin 17 at its rear end, as can be seen more clearly in FIG. 4. The pin 17 is in contact with the forward face of a ring 18, which is arranged inside a tubular sleeve 19, which is attached to the rear face of the rear coupling 3. Inside the sleeve 19 is arranged a helical compression spring 21, which is fitted between the rear face of the ring 18 and an internal flange 20 at the rear end of the sleeve 19. The ring 18, the sleeve 19 and the spring 21 are all arranged coaxially around the piston rod 1, and the force of the spring 21 strives to urge the ring 18 forward. This forward pressure acts on the pin 17 of the inner lever 15 and 16 and in its turn strives to rotate the eccentric 12 in such a way that the coupling 3 is locked to the piston rod 1.

Preferably there is an inner lever arm 15 and 16 with a corresponding pin 17 arranged at each end of the axis 13, such that there is one inner lever arm on each side of the clamping block 5. This can be seen more clearly in FIG. 4.

For releasing the rear coupling 3 from the piston rod 1, an external ring 22 is arranged around the rear coupling 3 in front of the radial pins 17 protruding from the inner levers 15 and 16. This ring 22 is connected to a yoke 23, and by means of this yoke 23, the ring 22 may be displaced rearwards against the force of an injection spring 24, which is arranged between the rear face of the ring 22 and the front face of stopping means 25. Thus, the injection spring 24 strives to move the ring 22 and the yoke 23 forwards in relation to the stopping means 25, but this forward movement is restricted by the lugs 26 and 27 on the rear clamping shoe 5. The stopping means 25 are connected to the holder device (not shown) in such a way that they can be fixed in a predetermined position in relation to said holder device. This setting of the position of the stopping means 25 determines the distance A between the rear end flange 20 of the sleeve 19 and the stopping means 25, and by this also the distance that the piston rod 1 travels forward when a dose is administered.

FIG. 2 shows the device of the invention where the rear coupling 3 has been moved rearward such that the sleeve 19 at its rear face abuts the stopping means 25.

In its new rear position, the rear coupling 3 has been locked to the piston rod 1 by means of the compression spring 21 which urges the ring 18 forward against the pins 17, which in turn move the inner lever arm 15 forward to rotate the eccentric disk 12 such that the clamping shoe 5 is locked to the piston rod 1. The rear coupling 3 is now situated at a longitudinal distance A from the front coupling 2 which is the same as the distance A shown in FIG. 1 between the sleeve 19 and the stopping means 25, and the injection spring 24 has been cocked. The device is now ready for the administering of an injection.

FIG. 3 shows schematically the device of the invention after an injection has been administered and an emptied injection cartridge is to be replaced with a fresh one. When the injection has been administered, the rear coupling 3 and the piston rod 1 have moved forward such that the rear coupling 3 rests against the stationary front coupling 2. In the figure, it is shown how the forward part of the piston rod 1 extends into the injection cartridge 28. The rear end of this injection cartridge is in contact with a sensor arm 29, which is urged against said rear end by means of a compression spring 32. The sensor arm 29 is also connected to an actuating slide 31, which is provided with two inclined surfaces 34 and 35. These two surfaces 34 and 35 may be brought into contact with the outer lever arms 8 and 14 by means of the spring 32, but as long as the sensor arm 29 is held back by the rear end of the injection cartridge 28, they are not in contact with said lever arms 8 and 14.

FIG. 4 is a schematic view of the device of the invention along the line IV—IV in FIG. 1. The piston rod 1 is here seen in section and surrounded by the clamping shoe 5 of the rear coupling 3. The piston rod 1 has a wedge-shaped cross-section, and the cross-section of the groove 6 in the clamping shoe 5 is also wedge-shaped and adapted to that of the piston rod 1. The piston rod 1 and the clamping shoe 5 are forced together by the action of the eccentric disk 12 which is manoeuvred by the outer lever arm 14 or the inner lever arm 15, which can be rotated around the axis 13. The rear ends of the inner lever arms 15 and 16 are provided with radial pins 17.

For moving the rear coupling 3 rearwards, there is provided a ring 22 connected with the yoke 23. The ring 22 is not completely circular, but has two diametrically opposed straight parts which are situated in front of the two pins 17 (only one of these straight parts is shown in the drawing). The ring 22 is acted on by the compression spring 24, of which only a part is shown. The spring 24 strives to move the ring 22 forward, but this movement is restricted by the lugs 26 and 27 on the clamping shoe 5.

The function of the device of the invention will now be described in detail, reference being made to the figures of the drawing:

In FIG. 1, the device is shown before it has been readied for an injection. This may be the first injection from a fresh injection cartridge, or a number of injections may already have been administered. The movable rear coupling 3 rests against the stationary front coupling 2 and the piston rod 1 is firmly locked to both couplings 2 and 3. In the front coupling 2, the spring 11 pulls the inner lever arm forwards, and this movement will rotate the eccentric disk 7 such that the piston rod 1 is urged into the groove 6 of the clamping shoe 4. In the rear coupling 3, the spring 21 in the sleeve 19 will push the ring 18 forward to act on the pins 17 and in this way turn the inner lever arm 5 in the forward direction. This will make the eccentric disk 12 rotate around the axis 13 to urge the piston rod 1 into the groove 6 of the clamping shoe 5.

The rear end 20 of the sleeve 19 on the rear coupling 3 is situated at a predetermined distance, A, from the stopping device 25. This distance A may be set to a predetermined value by moving the stopping device 25 in the longitudinal direction, and it determines the stroke of the piston in the injection cartridge at the administering. This setting should therefore not be easy to change unintentionally.

To move the rear coupling rearward, the user pulls the yoke 23 rearwards. The ring 22 connected with the yoke 23 will then move rearwards and will then also act on the pins 17 on the inner lever arms 15 and 16 against the pressure of the spring 21 on the ring 18 inside the sleeve 19. This will make the inner lever arm 15 turn in the rearward direction such that the eccentric disk 12 will also rotate around the axis 13 to release the clamping shoe 5 from the piston rod 1. The rear coupling 3 will then be free to follow the ring 22 and the yoke 23 in their movement rearwards against the pressure of the injection spring 24. This rearward movement is ended when the rear end of the sleeve 19 abuts against the stopping device 25, and when the rearward-directed pressure on the pins 17 is released, the spring 21 and the ring 18 inside the sleeve 19 will again urge the pins 17 forward. Through the intermediary of the inner lever arm 15, the eccentric disk 12 will rotate around the axis 13 in a direction to lock the piston rod 1 and the rear coupling 3 securely together. The injection spring 24 is now cocked and the device is ready for administering an injection, as is shown in FIG. 2.

When an injection is to be administered, the outer lever arm 8 of the front coupling 2 is moved inwards in the radial direction. This movement causes the eccentric disk 7 to rotate around the axis 9, such that the piston rod 1 is released from the clamping shoe 4 of the stationary front coupling. 2. The force of the cocked injection spring 24 will now propel the piston rod 1 forward until the rear coupling 3 again abuts the front coupling 2. As the piston rod 1 abuts or is connected to the rear piston in the injection cartridge 28, said piston will be displaced a corresponding distance forward to expel a predetermined dose of the injectable preparation from the cartridge. The distance travelled by the piston rod is the distance A in FIG. 2, and is the same as the preset distance A shown in FIG. 1.

During the movement of the piston rod 1, the rear coupling 3 has been locked to said piston rod by means of the spring 21, which by means of the ring 18 and the inner lever arm 15 and 16 has made the eccentric disk 12 turn in a direction to lock the clamping shoe 5 and the piston rod 1 together.

It is to be noted that the administration is carried out by means of the injection spring 24 only, and the user will not have to make any special effort to expel the injectable preparation from the cartridge. This means that the device of the invention has certain auto-injecting properties, which is a valuable advantage of the invention. The user will only have to insert the injection needle at the site of the injection, and the injection itself will be effected by simply releasing the lock between the piston rod 1 and the front coupling 2.

The release of the piston rod 1 from the front coupling 2 by the movement of the outer lever arm 8 may be effected by a trigger mechanism of a suitable design. Such trigger mechanisms are well-known to those skilled in the art, and need not have to be described here in detail.

After the injection has been administered, the device is again in the state shown in FIG. 1. To prepare the device for a subsequent injection, the user will only have move the rear coupling 3 rearwards by means of the ring 22 and the yoke 23, as has been described in the foregoing. This process may be repeated as many times as desired, until the injection cartridge 28 has been emptied. In the preferred system for administering injections, there will be no residue left in the cartridge, as the doses have been set to this effect. This has been described in the introductory part of this specification.

FIG. 3 shows the device of the invention when an injection cartridge is to be replaced. It is seen that the rear end of the cartridge 28 rests against a sensor arm 29, which is spring loaded in the forward direction by means of the spring 32. The cartridge 28 may be removed, for instance by removing the front part of the holder device, such as by unscrewing it, from a rear part of said holder device. The cartridge can then be pulled out in the forward direction.

When the cartridge 28 is pulled out in the forward direction, the sensor arm 29 will also be moved forward by the action of the spring 24. The sensor arm 29 is connected to a releasing slide 31, which has two inclined surfaces 34 and 35 which will get into contact with the outer lever arms 8 and 14, respectively, such that these lever arms are moved inwards in the radial direction. This inward movement will also make the eccentric disks 7 and 12, respectively, rotate around the axes 9 and 13, respectively, such that the two couplings 2 and 3 are released from the piston rod 1. The piston rod 1 will then be freed and can be taken out from the device.

When a fresh injection cartridge is to be inserted into the device of the invention, the cartridge is first combined with the piston rod in such a way that said piston rod rests against the rear face of the rear movable wall or piston of the injection cartridge. The assembly of piston rod and cartridge is then inserted into the holder device in such a way that the piston rod 1 is inserted through the two couplings 2 and 3 and the cartridge is introduced until its rear end abuts the sensor arm 29 and has moved this arm rearward to a predetermined position. At this position, the inclined surfaces 34 and 35 of the slide 31 will no longer be in contact with the outer lever arms 8 and 14, respectively, and these lever arms will then be free to move outwards through the influence of the springs 11 and 21, respectively. Through the rotation of the eccentric disks 7 and 12, respectively, the couplings 2 and 3 will now lock to the piston rod 1, and the device can now be readied for further injections.

The device of the invention may be used for single-chamber or dual-chamber injection cartridges. With a single-chamber cartridge, the device is ready for administering injections immediately after a fresh cartridge has been inserted. With a dual-chamber cartridge, the components in the two chambers will first have to mixed before an injection can be administered. This can easily be carried out by making a suitable number of "dry-run" administerings to advance the rear piston in the dual-chamber cartridge to force the liquid component in the rear chamber over into the front chamber and advance the rear piston to its position for administering the mixed preparation.

As has been stated in the foregoing, the specification and the drawings in the present disclosure have primarily been directed to the characteristic features of the present invention, and the conventional features have been treated more superficially. Thus, for instance, the holder device for the administering mechanism of the invention and the injection cartridge have not been described in detail. It is within the competence of a person skilled in the art to design a suitable holder device once the expected functions of said holder device in combination with the present invention have been made clear. The injection cartridges used, of the single-chamber or dual-chamber type, are of a conventional design and often have standard dimensions, as is well-known to those skilled in the art.

The specific design of the various details of the device of the invention will not present any problems to those skilled in the art, once the inventive idea and the expected functions of said details has been understood. Also the selections of suitable materials is within the competence of those skilled in the art, and as examples of such materials may be mentioned stainless steel, glass and various rubber and plastic materials. It goes without saying that such materials must fulfill the stringent requirements for pharmaceutical and medical apparatus, and must, for instance, be able to withstand heat sterilizing by autoclaving.

The expression "liquid injectable preparation" in the present specification and claims is intended to encompass injectable solutions as well as injectable emulsions, suspensions and other dispersions suitable for parenteral injection.

It is to be noted that the embodiments of the present invention shown in the foregoing disclosure and drawings are only examples and do not serve to limit the invention in any way. Various modifications and variations are readily apparent to a person skilled in the art, and the invention is only restricted by the scope of the appended claims.

I claim:

1. An apparatus for use in an injection device for infinitely variably metering and administering a liquid preparation, which apparatus comprises:
   a) a holder device housing a multi-dose injection cartridge containing the preparation, the cartridge comprising a front wall provided with an outlet for discharge of the preparation and a movable wall, whereby movement of the moveable wall in a forward direction will move the preparation towards the front wall and expel it through the outlet;
   b) a piston rod arranged movably in relation to said holder device and adapted to engage and move the movable wall in the cartridge;
   c) a first coupling and a second coupling, each being individually arranged on said holder device to releasably grip said piston rod, said first coupling being arranged stationary in relation to said holder device and said second coupling being arranged movable in relation to said holder device and along said piston rod when being disengaged therefrom; and
   d) a spring arranged between said holder device and said second coupling and being biased to move said second coupling in said forward direction; and wherein:
      i) said piston rod has a wedge-shaped cross-section;
      ii) said first coupling and said second coupling each comprises a wedge-shaped groove, the cross-section of which being adapted to the cross-section of said piston rod; and
      iii) said first coupling and said second coupling each comprises locking means arranged to releasably force said piston rod into said groove, to lock said piston rod to said couplings.

2. An apparatus according to claim 1, characterized in that the holder device is provided with stopping means which limit a rearward movement opposite the forward direction of said second coupling, said stopping means being adjustable in the longitudinal direction such that said rearward movement may be set at a predetermined value.

3. An apparatus according to claim 2, characterized in that said yoke is provided for a rearward movement opposite the forward direction of said second coupling, said yoke being connected to the second coupling and its locking means in such a way that said second coupling is released from the piston rod as it is moved rearwards and is again locked to the piston rod after said movement is terminated.

4. An apparatus according to claim 2, characterized in that the locking means of the two couplings include a spring arranged to force said piston rod into said groove.

5. An apparatus according to claim 2, characterized in that said lever means comprise eccentric disks, rotatable around an eccentrically positioned axis within said coupling, which by being rotated lock the couplings to the piston rod, or release the couplings from said piston rod.

6. An apparatus according to claim 2, further comprising a sensing arm, arranged on said holder device and extending between a portion of said cartridge and said locking means for the first and second couplings, said sensing arm being arranged movable relative to said holder device between a locking position and an unlocking position, the locking position being occupied at the presence of said cartridge portion in said holder device and the unlocking position being occupied at the absence of said cartridge portion in said holder device, said sensing arm when in said locking position affecting the locking means to force said piston rod into said groove and when in said unlocking position affecting the locking means to release said piston rod from said groove.

7. Apparatus according to claim 1, characterized in that a yoke is provided for a rearward movement opposite the forward direction of said second coupling, said yoke being connected to the second coupling and its locking means in such a way that said second coupling is released from the piston rod as it is moved rearwards and is again locked to the piston rod after said movement is terminated.

8. An apparatus according to claim 7, characterized in that the locking means of the two couplings include a spring arranged to force said piston rod into said groove.

9. An apparatus according to claim 7, characterized in that said lever means comprise eccentric disks, rotatable around an eccentrically positioned axis within said coupling, which by being rotated lock the couplings to the piston rod, or release the couplings from said piston rod.

10. An apparatus according to claim 7, further comprising a sensing arm, arranged on said holder device and extending between a portion of said cartridge and said locking means for the first and second couplings, said sensing arm being arranged movable relative to said holder device between a locking position and an unlocking position, the locking position being occupied at the presence of said cartridge portion in said holder device and the unlocking position being occupied at the absence of said cartridge portion in said holder device, said sensing arm when in said locking position affecting the locking means to force said piston rod into said groove and when in said unlocking position affecting the locking means to release said piston rod from said groove.

11. Apparatus according to claim 1 characterized in that the locking means of the two couplings include a spring arranged to force said piston rod into said groove.

12. An apparatus according to claim 11, characterized in that said lever means comprise eccentric disks, rotatable around an eccentrically positioned axis within said coupling, which by being rotated lock the couplings to the piston rod, or release the couplings from said piston rod.

13. An apparatus according to claim 11, further comprising a sensing arm, arranged on said holder device and extending between a portion of said cartridge and said locking means for the first and second couplings, said sensing arm being arranged movable relative to said holder device between a locking position and an unlocking position, the locking position being occupied at the presence of said cartridge portion in said holder device and the unlocking position being occupied at the absence of said cartridge portion in said holder device, said sensing arm when in said locking position affecting the locking means to force said piston rod into said groove and when in said unlocking position affecting the locking means to release said piston rod from said groove.

14. Apparatus according to claim 1 characterized in that said locking means comprise eccentric disks, rotatable around an eccentrically positioned axis within said coupling, which by being rotated lock the couplings to the piston rod, or release the couplings from said piston rod.

15. An apparatus according to claim 1, further comprising a sensing arm, arranged on said holder device and extending between a portion of said cartridge and said locking means for the first and second couplings, said sensing arm being arranged movable relative to said holder device between a locking position and an unlocking position, the locking position being occupied at the presence of said cartridge portion in said holder device and the unlocking position being occupied at the absence of said cartridge portion in said holder device, said sensing arm when in said locking position affecting the locking means to force said piston rod into said groove and when in said unlocking position affecting the locking means to release said piston rod from said groove.

16. An apparatus for use in an injection device for infinitely variably metering and administering a liquid preparation, which apparatus comprises:
   a) a holder device housing a multi-dose injection cartridge containing the preparation, the cartridge comprising a front wall provided with an outlet for discharge of the preparation and a movable wall, whereby movement of the moveable wall in a forward direction will move the preparation towards the front wall and expel it through the outlet;
   b) a piston rod arranged movably in relation to said holder device and adapted to engage and move the movable wall in the cartridge;
   c) at least one coupling being arranged on said holder device to releasably grip said piston rod, said at least one coupling being arranged movably in relation to said holder device and along said piston rod when being disengaged therefrom; and
   d) stopping means arranged permanently or adjustably fixed in relation to said holder device and being positioned relative to said at least one coupling so as to limit movement of said coupling between predetermined positions; and wherein:
      i) said piston rod has a wedge-shaped cross-section;
      ii) said at least one coupling comprises a wedge-shaped groove, the cross-section of which being adapted to the cross-section of said piston rod; and
      iii) said at least one coupling comprises locking means arranged to releasably force said piston rod into said groove, to lock said piston rod to said coupling.

17. An apparatus according to claim 16, characterized in that the locking means of said at least one coupling include a spring arranged to force said piston rod into said groove.

18. An apparatus according to claim 16, characterized in that said locking means comprise eccentric disks, rotatable around an eccentrically positioned axis, which by being rotated lock said at least one coupling to said piston rod, or release said at least one coupling from said piston rod.

19. An apparatus according to claim 16, further comprising a sensing arm, arranged on said holder device and extending between a portion of said cartridge and said locking means for the at least one coupling, said sensing arm being arranged movable relative to said holder device between a locking position and an unlocking position, the locking position being occupied at the presence of said cartridge portion in said holder device and the unlocking position being occupied at the absence of said cartridge portion in said holder device, said sensing arm when in said locking position affecting the locking means to force said piston rod into said groove and when in said unlocking position affecting the locking means to release said piston rod from said groove.

* * * * *